United States Patent [19]

Yoshioka et al.

[11] Patent Number: 4,517,127
[45] Date of Patent: May 14, 1985

[54] β-LACTAM DERIVATIVES AND PROCESS FOR PRODUCTION THEREOF

[75] Inventors: Takeo Yoshioka, Ayase; Kenichi Yamamoto, Fujisawa; Yasuo Fukagawa, Kamakura; Yasutaka Shimauchi, Kanagawa; Tomoyuki Ishikura, Chigasaki, all of Japan

[73] Assignee: Sanraku-Ocean Co., Ltd., Tokyo, Japan

[21] Appl. No.: 559,681

[22] Filed: Dec. 9, 1983

[30] Foreign Application Priority Data

Dec. 10, 1982 [JP] Japan .................................. 57-215539

[51] Int. Cl.³ ..................... C07D 487/04; A61K 31/40
[52] U.S. Cl. ......................... 260/245.2 T; 260/245.2 R
[58] Field of Search ................. 260/245.2 T, 245.2 R; 424/274

[56] References Cited

U.S. PATENT DOCUMENTS 4,321,197  3/1982  Cama et al. .................. 260/245.2 T
4,424,230  1/1984  Christensen et al. ......... 260/245.2 T Primary Examiner—Nicholas S. Rizzo
Attorney, Agent, or Firm—Wenderoth, Lind & Ponack

[57] ABSTRACT

A compound represented by the following formula:

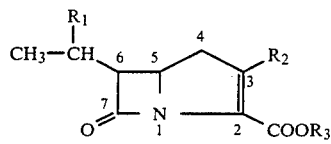

wherein $R_1$ represents a hydrogen atom or a hydroxyl group, $R_2$ represents a group of the formula $-CH_2NO_2$, $-CN \rightarrow O$ or

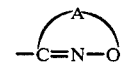

in which A represents a group of the formula

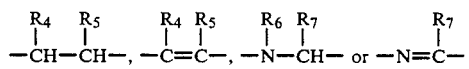

in which $R_4$ represents a hydrogen atom or an alkoxycarbonyl group, $R_5$ represents a phenyl, alkoxycarbonyl or alkanoyloxymethyl group, $R_6$ represents an alkyl group and $R_7$ represents a phenyl, naphthyl, pyridyl, furyl or thienyl group; and $R_3$ represents a hydrogen atom or a substituted or unsubstituted hydrocarbon group, and a process for production thereof.

3 Claims, No Drawings

β-LACTAM DERIVATIVES AND PROCESS FOR PRODUCTION THEREOF

This invention relates to novel compounds having a 7-oxo-1-azabicyclo[3.2.0]hept-2-ene-2-carboxylic acid skeleton. More particularly, this invention relates to compounds represented by the following formula

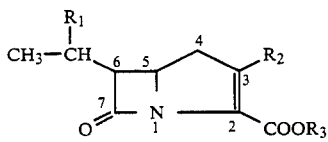
(I)

wherein $R_1$ represents a hydrogen atom or a hydroxyl group, $R_2$ represents a group of the formula $-CH_2NO_2$, $-CH\!=\!\!O$ or

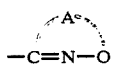

in which A represents a group of the formula

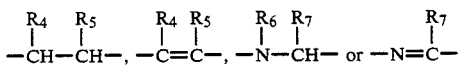

in which $R_4$ represents a hydrogen atom or an alkoxycarbonyl group, $R_5$ represents a phenyl, alkoxycarbonyl or alkanoyloxymethyl group, $R_6$ represents an alkyl group and $R_7$ represents a phenyl, naphthyl, pyridyl, furyl or thienyl group; and $R_3$ represents a hydrogen atom or a substituted or unsubstituted hydrocarbon group; and to a process for production thereof.

The compounds of formula (I) are novel compounds not described in the prior literature. Particularly compounds of formula (I) in which $R_2$ is $-CH_2NO_2$ or

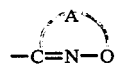

have excellent antibacterial activity against various pathogenic microorganisms and have the ability to increase the antibacterial activity of known β-lactam antibiotics against β-lactamase-producing microorganisms. Hence, they can be used as an active ingredient of antibacterial agents or agents for increasing their antibacterial activity for the prevention, therapy and/or treatment of bacterial infections.

Compounds of formula (I) in which $R_2$ is $-CN\!=\!\!O$ have high reactivity, and can be used as intermediates for the synthesis of compounds of formula (I) in which $R_2$ is

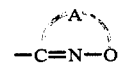

and other carbapenem derivatives having excellent antibacterial activity and high utility.

The compounds of formula (I) have two or three asymmetric carbon atoms in total, i.e. the carbon atoms at the 5- and 6-positions of the carbapenem skeleton, and the carbon atom at the 1-position of the side chain at the 6-position in the case of $R_1$ being a hydroxyl group. Accordingly, the compounds of formula (I) can exist as the individual diastereomers or a mixture of two or more diastereomers. From the viewpoint of antibacterial activity, however, the carbon atoms at the 5- and 6-positions of the carbapenem skeleton desirably have 5R- and 6R- or 6S-configurations. Compounds of formula (I) in which $R_1$ is a hydroxyl group desirably have a three-dimensional structure represented by the following formula

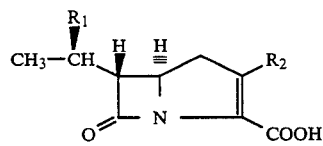

The "alkyl group" and the alkyl moiety in the "alkoxycarbonyl group" and "alkanoyloxymethyl group", as used in the present specification, may be linear or branched. Generally, those having not more than 6 carbon atoms, preferably not more than 4 carbon atoms, are suitable. Examples of the "alkyl group" are methyl, ethyl, propyl, isopropyl, butyl, isobutyl, sec-butyl, tert-butyl, pentyl and hexyl. Examples of the "alkoxycarbonyl group" include methoxycarbonyl, ethoxycarbonyl and isopropoxycarbonyl. Examples of the "alkanoyloxymethyl group" include acetyloxymethyl, propionyloxymethyl and isovaleryloxymethyl.

The term "lower", as used in this application, means that a group or compound qualified by it has not more than 6 carbon atoms, preferably not more than 4 carbon atoms.

$R_3$ in the carboxy side chain at the 2-position of the compounds of formula (I) is a hydrogen atom or an ester residue. Specifically, the ester residue includes the following substituted or unsubstituted hydrocarbon groups.

(1) Substituted or unsubstituted alkyl, alkenyl or alkynyl.
(2) Cycloalkyl.
(3) Cycloalkyl-alkyl.
(4) Substituted or unsubstituted aryl.
(5) Substituted or unsubstituted aralkyl.
(6) Heterocyclic alkyl.

Of these, the "substituted or unsubstituted aralkyl groups" are especially preferred as the ester residue. The aryl moiety in the aralkyl groups may be monocyclic as in phenyl or bicyclic as in naphthyl. The alkyl moiety in these aralkyl groups is preferably lower. These aralkyl groups may usually have 7 to 25 carbon atoms, preferably 7 to 22 carbon atoms, and more preferably 7 to 19 carbon atoms. Examples of the unsubstituted aralkyl groups include benzyl, p-tert-butylbenzyl, p-methylbenzyl, 2,4-dimethylbenzyl, 2,4,6-trimethylbenzyl, benzhydryl, 1,1-diphenylethyl, 1,1-diphenylpropyl, 1,1-diphenylbutyl, trityl and p-methyltrityl. Suitable substituents on the aromatic ring of the substituted aralkyl groups include, for example, halogen atoms, lower alkoxy, aryloxy, lower haloalkyl, acyloxy (e.g., $C_1$-$C_{10}$ alkanoyloxy, aroyloxy), acylamino (e.g., lower alkanoylamino, aroylamino), carboxyl, lower alkoxycarbonyl, hydroxyl group and nitro. Thus, examples of the aralkyl groups substituted by these groups are p-chlorobenzyl, p-bromobenzyl, p-methoxybenzyl, p-tert-butoxybenzyl, 3,5-bis-tert-butoxy-4-hydroxybenzyl, m-phenoxybenzyl, p-trifluoromethylbenzyl, o- or p-pivaloyloxybenzyl, p-acetoxybenzyl, p-benzoyloxybenzyl, p-2-ethylhexanoylbenzyl, p-benzamidebenzyl, p-carboxybenzyl (including the case where the carboxy is in the form of its alkali metal salt), p-methoxycarbonylbenzyl, p-ethoxycarbonylbenzyl, p-butoxycarbonylbenzyl, p-hydroxybenzyl, o- or p-nitrobenzyl, p-chlorobenzhydryl, p-methoxybenzhydryl, p-acetoxybenzhydryl, p-nitrobenzhydryl, m- or p-chlorotrityl, p-bromotrityl, p-methoxytrityl, p-ethoxytrityl and p-nitrotolyl.

Typical examples of the compounds of formula (I) provided by this invention are shown in the following table in addition to those given in Examples.

TABLE

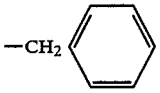 (I)

| No. | $R_1$ | $R_2$ | $R_3$ |
|---|---|---|---|
| 1. | H | $CH_2NO_2$ | H |
| 2. | H | $CH_2NO_2$ | 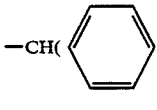 |
| 3. | H | $CH_2NO_2$ | 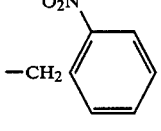 |
| 4. | H | $CH_2NO_2$ | 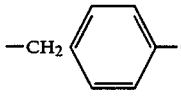 |
| 5. | H | $CH_2NO_2$ | 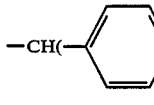 |
| 6. | H | $CH_2NO_2$ | 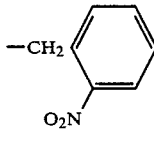 |
| 7. | H | $CH_2NO_2$ | 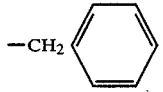 |
| 8. | OH | $CH_2NO_2$ | H |
| 9. | OH | $CH_2NO_2$ | 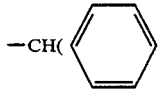 |
| 10. | OH | $CH_2NO_2$ | 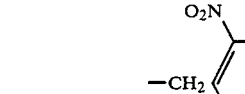 |
| 11. | OH | $CH_2NO_2$ | 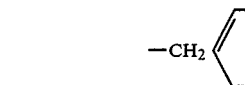 |
| 12. | OH | $CH_2NO_2$ | 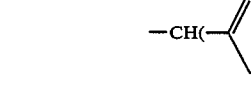 |
| 13. | OH | $CH_2NO_2$ |  |
| 14. | OH | $CH_2NO_2$ | 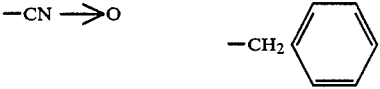 |
| 15. | H | $-CN \rightarrow O$ | H |
| 16. | H | $-CN \rightarrow O$ |  |
| 17. | H | $-CN \rightarrow O$ |  |
| 18. | H | $-CN \rightarrow O$ |  |
| 19. | H | $-CN \rightarrow O$ |  |
| 20. | H | $-CN \rightarrow O$ | 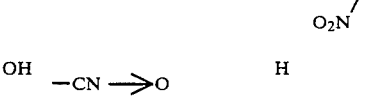 |
| 21. | H | $-CN \rightarrow O$ | |
| 22. | OH | $-CN \rightarrow O$ | H |

TABLE-continued $$\text{(I)}$$

Structure: β-lactam with CH$_3$-CH(R$_1$)- substituent and R$_2$, COOR$_3$ groups

| No. | R$_1$ | R$_2$ | R$_3$ |
|---|---|---|---|
| 23. | OH | —CN→O | —CH$_2$—C$_6$H$_4$—NO$_2$ |
| 24. | OH | —CN→O | —CH$_2$—C$_6$H$_5$ |
| 25. | OH | —CN→O | —CH(C$_6$H$_5$)$_2$ |
| 26. | OH | —CN→O | —CH$_2$—C$_6$H$_4$(o-NO$_2$) |
| 27. | OH | —CN→O | —CH$_2$—C$_6$H$_4$—Cl |
| 28. | OH | —CN→O | —CH(p-Cl-C$_6$H$_4$)$_2$ |
| 29. | OH | —CN→O | —CH$_2$—C$_6$H$_3$(NO$_2$)$_2$ |
| 30. | H | =C(CO$_2$CH$_3$)$_2$ group with N—O ring | H |
| 31. | OH | =C(CO$_2$CH$_3$)$_2$ group with N—O ring | H |
| 32. | H | CH(CO$_2$CH$_3$) with N—O ring | H |
| 33. | OH | CH(CO$_2$CH$_3$) with N—O ring | H |
| 34. | H | CH(CO$_2$C$_2$H$_5$) with N—O ring | H |
| 35. | OH | CH(CO$_2$C$_2$H$_5$) with N—O ring | H |
| 36. | H | CH(CO$_2$C$_2$H$_5$) with N—O ring | —CH$_2$—C$_6$H$_4$—NO$_2$ |
| 37. | OH | CH(CO$_2$C$_2$H$_5$) with N—O ring | —CH$_2$—C$_6$H$_4$—NO$_2$ |
| 38. | OH | CH(CO$_2$C$_3$H$_7$) with N—O ring | H |
| 39. | H | =C(CO$_2$CH$_3$)$_2$ with N—O ring | —CH$_2$—C$_6$H$_4$—NO$_2$ |
| 40. | OH | =C(CO$_2$CH$_3$)$_2$ with N—O ring | —CH$_2$—C$_6$H$_4$—NO$_2$ |
| 41. | H | C$_6$H$_5$-substituted with N—O ring | —CH$_2$—C$_6$H$_4$—NO$_2$ |

TABLE-continued $$\begin{array}{c} R_1 \\ | \\ CH_3-CH \end{array} \diagdown \diagup R_2 \atop O=\phantom{X}N\diagdown COOR_3 \qquad (I)$$

| No. | R₁ | R₂ | R₃ |
|---|---|---|---|
| 42. | OH | 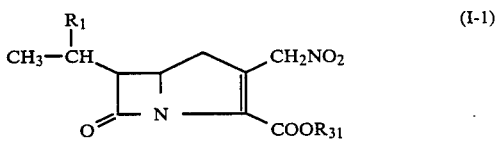 | $-CH_2-\phenyl-NO_2$ |
| 43. | H | (CH₃ group with N-O, phenyl) | $-CH_2-\phenyl-NO_2$ |
| 44. | OH | (CH₃ group with N-O, phenyl) | $-CH_2-\phenyl-NO_2$ |
| 45. | H | 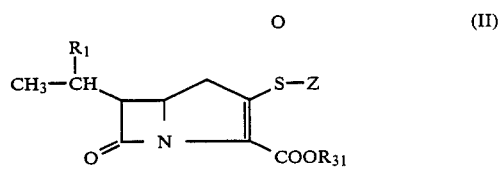 | $-CH_2-\phenyl-NO_2$ |
| 46. | OH | (CH₂CH₃ group with N-O, pyridyl) | $-CH_2-\phenyl-NO_2$ |
| 47. | H | 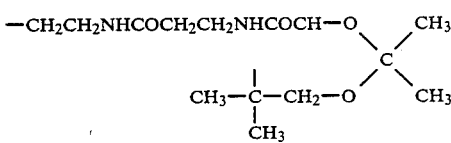 | $-CH_2-\phenyl-NO_2$ |
| 48. | OH | (CH₃ group with N-O, furyl) | $-CH_2-\phenyl-NO_2$ |

Compounds of formula (I) in which $R_3$ is a hydrogen atom can exist in the form of salts. Examples of the salts include alkali metal salts such as sodium, potassium and lithium salts; alkaline earth metal salts such as calcium and magnesium salts; salts with other metals such as aluminum salts; ammonium salts; salts with primary, secondary or tertiary amines such as monoethylamine, dimethylamine, trimethylamine, monoethanolamine and diethanolamine salts; and salts with other organic bases such as benzathine and procaine salts. Of these examples, pharmaceutically acceptable salts are preferred. Above all, the alkali metal salts such as sodium and potassium salts are preferred.

A preferred group of the compounds of formula (I) provided by this invention is $-CH_2NO_2$ as $R_2$. Above all, compounds of this group in which $R_3$ is a hydrogen atom or a substituted or unsubstituted aralkyl group are preferred.

According to this invention, compounds of formula (I) in which $R_2$ is $-CH_2NO_2$, i.e.

$$\begin{array}{c} R_1 \\ | \\ CH_3-CH \end{array} \diagdown \diagup CH_2NO_2 \atop O=\phantom{X}N\diagdown COOR_{31} \qquad (I\text{-}1)$$

wherein $R_{31}$ represents a substituted or unsubstituted hydrocarbon group and $R_1$ is as defined above, can be produced by reacting a compound of the formula $$\begin{array}{c} R_1 \\ | \\ CH_3-CH \end{array} \diagdown \diagup S-Z \atop O=\phantom{X}N\diagdown COOR_{31} \qquad (II)$$

wherein Z represents a group of the formula $-CH_2CH_2NHCOCH_3$ or a group of the formula $$-CH_2CH_2NHCOCH_2CH_2NHCOCH-O\diagdown \atop CH_3-\underset{\underset{CH_3}{|}}{\overset{|}{C}}-CH_2-O\diagup\overset{CH_3}{\underset{CH_3}{C}}$$

and $R_1$ and $R_{31}$ are as defined above, with nitromethane in the presence of a base.

The reaction of the compound of formula (II) with nitromethane can be carried out usually in the absence of solvent using a large excess of nitromethane. As required, it may be carried out in a polar solvent such as N,N-dimethylformamide (DMF), tetrahydrofuran (THF), 1,4-dioxane, hexamethylphosphoramide (HMPA) and glyme. In the case of using the solvent, the proportion of nitromethane is desirably at least 1 mole, preferably 10 to 100 moles, per mole of the compound of formula (II).

The above reaction can be terminated in about 15 minutes to about 3 hours at a temperature of generally about $-50°$ C. to about $80°$ C., preferably about $-30°$ C. to room temperature.

The reaction is carried out in the presence of a base. Examples of bases which can be used in this invention are organic bases such as tetramethylguanine, 2-dimethylamino-1-pyrrone, 1,4-diazabicyclo[2.2.2]octane, 1,5-diazabicyclo[3.4.0]nonene-5 (DBN), 1,5-diazabicyclo[5.4.0]undecene-5 (DBU) and triethylamine. Of these bases, tetramethylguanidine, DBN and DBU are advantageously used. The amount of the base is not limited in particular. Its suitable amount is generally at least 0.5 mole, preferably 1 to 5 moles, per mole of the compound of formula (II).

Thus, the compound of formula (I-1) is formed in a good yield. This compound can be isolated from the reaction mixture by known methods, for example, by extraction with an organic solvent, or column chromatography using silica gel, Bio-beads (a product of Bio-Rad Laboratories) and Sephadex LH-20 (a product of Pharmacia Fine Chemicals AB). If desired, without isolating it, the reaction mixture can be directly subjected to a reaction to be described hereinafter.

The starting compounds of formula (II) in which Z represents a group of the formula —$CH_2CH_2NHCOCH_3$ are known compounds described, for example, in U.S. Pat. No. 4,337,199.

Compounds of formula (II) in which Z represents a group of the formula

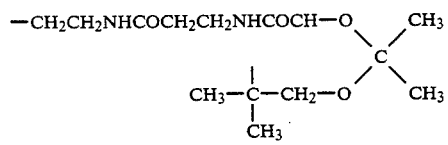

are novel. These novel compounds can be easily produced by ketalizing in a manner known per se the hydroxyl groups at the $\alpha$- and $\gamma$-positions of the pantoyl group of the known antibiotics OA-6129A, OA-6129B1 or OA-6129B2 described, for example, in European Laid-Open Patent Application No. 48999A1, and then oxidizing the products as described in U.S. Pat. No. 4,337,199.

According to this invention, the compounds of formula (I-1) produced by the method described hereinabove can be dehydrated to compounds of formula (I) in which $R_2$ is —CH O, i.e. compounds of the following formula (I-2)

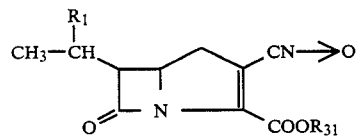

wherein $R_1$ and $R_{31}$ are as defined above.

Dehydration of the compounds of formula (I-1) can be carried out with a dehydrating agent in the aforesaid polar solvent. Examples of the dehydrating agent that can be used include acid chlorides such as methyl chloroformate, acetyl chloride, phosphorus oxychloride and thionyl chloride; and isocyanates such as phenyl isocyanate. The amount of the dehydrating agent is not particularly restricted. Preferably, it is used in an amount of at least 1 equivalent, preferably 1.2 to 2 equivalents, per mole of the compound of formula (I-1).

The reaction temperature may be generally about —50° C. to room temperature, preferably about —20° C. to about 0° C. At this temperature, the reaction can be terminated in about 15 minutes to about 3 hours.

The compounds of formula (I-1) can be obtained in a good yield. They can be isolated by the method exemplified above, or can be subjected to a subsequent reaction without isolation.

By reacting the compounds of formula (I-2) further with compounds represented by the formulas

| $R_4$—CH=CH—$R_5$ | (III) |
| $R_4$—C≡C—$R_5$ | (IV) |

-continued

| $R_6$—N=CH—$R_7$ | (V) |
| or | |
| $R_7$—C≡N | (VI) | wherein $R_4$, $R_5$, $R_6$ and $R_7$ are as defined above, compounds of formula (I) in which $R_2$ represents

i.e. compounds of the following formula

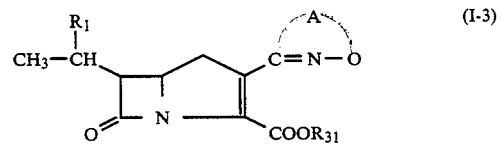

wherein $R_1$, $R_{31}$ and A are as defined above, can be obtained.

The reaction of the compounds of formula (I-2) with the compounds of formula (III), (IV), (V) or (VI) usually proceeds almost quantitatively at a temperature of about —20° C. to about 80° C., preferably about 0° C. to room temperature, in the aforesaid aprotic polar solvent.

The amount of the compound of formula (III), (IV), (V) or (VI) is not particularly restricted, but advantageously, it is used in an amount of generally at least 1 mole, preferably 1.5 to 10.0 moles, per mole of the compound of formula (I-1).

The resulting compounds of formula (I-3) can be isolated from the raction mixture by purifying in a manner known per se, for example, by diluting the reaction mixture with an organic solvent such as benzene, toluene, ethyl acetate and diethyl ether, washing the diluted raction mixture with water or phosphate buffer, optionally concentrating it, and subjecting it to column chromatography using silica gel, alumina, Bio-beads, Sephadex LH-20 either singly or in combination.

The compounds to be reacted with the compounds of formula (I-2) in the above reaction may be any compound which belongs to so-called dipolarophiles. The compounds of formula (III), (IV), (V) or (VI) are typical of these compounds. These compounds are generally known, or even those which are novel can be synthesized by similar methods to those used to prepare the known compounds. Typical examples of the compounds of formula (III), (IV), (V) or (VI) which can be used in the above reaction are shown below.

Compounds of formula (III)

Various esters such as acrylic esters, methacrylic esters, fumaric esters and cinnamic esters.

Compounds of formula (IV)

Various esters such as acetylenedicarboxylic acid esters acetylenemonocarboxylic acid esters and esters of propargyl alcohol and phenylacetylene.

Compounds of formula (V)

Schiff bases such as alkylidenealkylamines, benzylidenealkylamines, pyridylmethylidenealkylamines, furylmethylidenealkylamines and thienylmethylidenealkylamines.

Compounds of formula (VI)

Aromatic nitrile derivatives such as benzonitrile, naphthyl nitrile and pyridylnitrile.

The resulting compounds of formula (I) in which $R_3$ is a substituted or unsubstituted hydrocarbon group can be converted to the corresponding compounds of formula (I) in which $R_3$ is a hydrogen atom, for example, by treatment with horse blood or by hydrogenolysis. Compounds of formula (I) in which $R_3$ is a hydrogen atom can be converted to salts of above-exemplified types by a customary method.

The compounds of formula (I) provided by this invention, particularly the compounds of formula (I-1) or (I-3), have excellent antibacterial activity, and their antibacterial activity can be determined by a known method of measuring antibacterial activity using an agar plate. The antibacterial activity of the esters of the above compounds can be assayed as such by adding 10% horse blood to an assay medium in the preparation of the agar plate.

The following Examples illustrate the present invention in greater detail.

In these Examples, the following abbreviations are used.
Bzl: benzyl group
pNB: p-nitrobenzyl group
PS-5: 3-(2-acetamidoethyl)thio-6-ethyl-7-oxoazabicyclo-[3.2.0]hept-2-ene-2-carboxylic acid
OA-6129A: 6-ethyl-3-pantetheinyl-7-oxo-1-azabicyclo[3.2.0]-hept-2-ene-2-carboxylic acid
OA-6129B$_2$: 5,6-trans-3-pantetheinyl-6-(1-hydroxyethyl)-7-oxo-1-azabicyclo[3.2.0]hept-2-ene-2-carboxylic acid

EXAMPLE 1

Introduction of the isopropylidene group into p-nitrobenzyl ester of antibiotic OA-6129B$_2$ Twenty milligrams of p-nitrobenzyl ester of antibiotic OA-6129B$_2$ obtained by the method of Example 5 of European Laid-Open Patent Application No. 4899A1 cited hereinabove was dissolved in a mixture of 5.0 ml of acetone, 2.0 ml of 2,2-dimethoxypropane and 100 mg of anhydrous sodium sulfate. With stirring at room temperature, 0.5 mg of p-toluenesulfonic acid was added. After reaction for 30 minutes, 6 μl of triethylamine was added to the reaction mixture, and the mixture was stirred for 5 minutes. The reaction mixture was evaporated under reduced pressure, and 30 ml of methylene chloride was added to the residue. The mixture was then washed with 20 ml of 0.1M phosphate buffer (pH 8.4), and the organic layer was dehydrated with anhydrous sodium sulfate and evaporated under reduced pressure. The residue was dissolved in a small amount of methylene chloride and adsorbed on a column of 2 g of silica gel filled with benzene/acetone (2/1). The column was successively developed with benzene/acetone mixtures at mixing ratios of 2/1, 1/1 and 1/2. Fractions which were eluted with benzene/acetone (1/1) and benzene/acetone (1/2) were collected and concentrated to give 6.6 mg of O-isopropylidene p-nitrobenzyl ester of antibiotic OA-6129B$_2$ which showed an Rf value of 0.64 in silica gelatin-layer chromatography developed with benzene/acetone (1/4).

The physico-chemical properties of this compound are as follows:
(1) Specific rotation: $[\alpha]_D^{24}$: 55.1° (c=0.5, CH$_2$Cl$_2$).
(2) UV spectrum: $\lambda_{max}^{CH2Cl2}$ nm($\epsilon$): 319 (9700), 270 (11900).
(3) IR spectrum: $\nu_{max}^{CHCl3}$ cm$^{-1}$: 1778 ($\beta$-lactam), 1700 (ester), 1668 (amide).

EXAMPLE 2

S-Oxidation of O-isopropylidene p-nitrobenzyl ester of antibiotic OA-6129B$_2$ 110 mg of O-isopropylidene p-nitrobenzyl ester of antibiotic OA-6129B$_2$ was dissolved in 7.7 ml of methylene chloride, and the solution was cooled to −30° C. A methylene chloride solution containing 42.9 mg of m-chloroperbenzoic acid was added dropwise, and they were reacted at the above temperature for 30 minutes. The reaction mixture was poured into 20 ml of methylene chloride, and washed with a saturated aqueous solution of sodium hydrogen carbonate and then with phosphate buffer (pH 6.80). The organic layer was dehydrated over anhydrous sodium sulfate, and concentrated under reduced pressure. The residue was adsorbed on a column of 5 g of silica gel filled with benzene/acetone (2/1). The column was eluted with benzene/acetone mixtures at mixing ratios of 1/1, 1/3 and 1/10. Fractions which showed an ultraviolet absorption (wavelength 2537 Å) at an Rf value of 0.24 in silica gel thin-layer chromatography developed with benzene/acetone (1/3), and concentrated to dryness under reduced pressure to give 81.8 mg of the S-oxide having the following physico-chemical properties.
(1) Specific rotation: $[\alpha]_D^{23.5}$: 18.5° (c=1.0, CHCl$_3$).
(2) UV spectrum: $\lambda_{max}^{CHCl3}$ nm($\epsilon$): 314 (7400), 268 (12100).
(3) NMR spectrum [CDCl$_3$, δ(ppm)]

0.97 (3H, s, CH$_3$—C(CH$_3$)—), 1.04 (3H, s, CH$_3$—C(CH$_3$)—), 1.37 (3H, d, J = 7.0 Hz, CH$_3$—CH—), 1.43 (6H, m, O—C(CH$_3$)(CH$_3$)—O), 2.41 (2H, t, J = 6.5 Hz, CO—CH$_2$—CH$_2$—NH),
2.80–3.80 (11H, m, S—CH$_2$—CH$_2$—NH, CO—CH$_2$—CH$_2$—NH, C—4H$_2$, C—6H, C—CH$_2$—O),
4.03 (1H, s, O—CH—CO),
4.00–4.50 (2H, m, C—5H, C—8H), 5.19 (1H, d, J = 14.5 Hz, —CH(H)—Ar), 5.46 (1H, d, J = 14.5 Hz, —CH(H)—Ar), 6.17 (1H, m, NH),
6.95 (1H, m, NH),
7.67 (2H, m, Ar.H),
8.17 (2H, d, Ar.H).

MS (FD): m/z 687 (M+Na), 665 (M+1).

EXAMPLE 3 p-Nitrobenzyl 6-ethyl-3-nitromethyl-7-oxo-1-azabicyclo[3.2.0]hept-2-ene-2-carboxylate

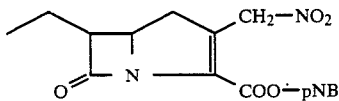

100 mg (0.22 mmole) of PS-5.p-nitrobenzyl S-oxide was dissolved in 10 ml of nitromethane, and the solution was cooled to −25° C. Then, 140 μl (1.1 mmoles) of tetramethylguanidine was added. They were reacted at the above temperature for 30 minutes, and then 132 μl (2.2 mmoles) of acetic acid was added. The reaction mixture was poured into 70 ml of ethyl acetate, and washed three times with water. The organic layer was dried over anhydrous sodium sulfate, and filtered. The filtrate was concentrated under reduced pressure to 2 ml. The concentrate was immediately charged onto a column of Bio-beads (1.2 cm×90 cm), and the column was developed with benzene. Fractions which showed an ultraviolet absorption at an Rf of 0.42 in silica gel thin-layer chromatography developed with benzene/ethyl acetate (3/1) were collected, and concentrated to dryness under reduced pressure to give 48 mg (yield 58%) of the title compound having the following physico-chemical properties:

(1) IR spectrum $\nu_{max}^{CHCl_3}$ cm$^{-1}$: 1780 (β-lactam), 1725 (ester), 1555, 1520, 1350 (nitro).

(2) UV spectrum $\lambda_{max}^{CHCl_2}$ nm(ε): 268 (12100).

(3) NMR spectrum (CDCl$_3$, TMS)δ: 1.07 (3H, t, J=7.0 Hz, CH$_3$—CH$_2$), 1.65–2.00 (2H, m, CH$_3$—CH$_2$), 3.02 (2H, d like, J=9.0 Hz, C—4 Hz), 3.22 (1H, m, C—6H), 4.02 (1H, dt, J=3.0 Hz, J=9.0 Hz, C—5H), 5.22 (1H, d, J=14.0 Hz, C$\underline{H}$H—Ar), 5.31 (1H, d, J=15.5 Hz, C$\underline{H}$H—NO$_2$), 5.49 (1H, d, J=14.0 Hz, CH$\underline{H}$—Ar), 5.78 (1H, d, J=15.5 Hz, CH$\underline{H}$—NO$_2$), 7.64 (2$\underline{H}$, d, J=8.5 Hz, Ar.$\underline{H}$), 8.20 (2H, d, J=$\overline{8.5}$ Hz, Ar.$\underline{H}$).

This compound was also obtained by treating S-oxide of p-nitrobenzyl ester of OA-6129A under the aforesaid conditions.

EXAMPLE 4

Benzyl 6-ethyl-3-nitromethyl-7-oxo-1-azabicyclo[3.2.0]hept-2-ene-2-carboxylate

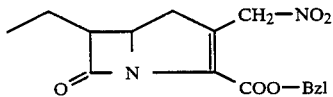

The S-oxide of benzyl ester of PS-5 (5 mg) was dissolved in 2 ml of nitromethane, and at −25° C., 7 μl of tetramethylguanidine was added. They were reacted at the above temperature for 30 minutes. The reaction mixture was worked up in the same way as in Example 3. Fractions which showed an ultraviolet absorption at an Rf value of 0.78 in silica gel thin-layer chromatography developed with benzene/acetone (3/2) were collected, and concentrated to dryness under reduced pressure to give 2.5 mg of the title compound.

(1) IR spectrum $\nu_{max}^{CHCl_3}$ cm$^{-1}$: 1785 (β-lactam), 1725 (ester), 1560, 1340 (nitro).

EXAMPLE 5 p-Nitrobenzyl 6-(1-hydroxyethyl)-3-nitromethyl-7-oxo-1-azabicyclo[3.2.1]hept-2-ene-2-carboxylate

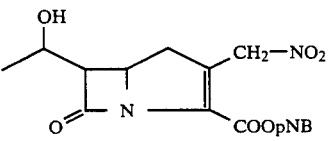

44.6 mg (0.07 mmole) of an S-oxide of p-nitrobenzyl ester of isopropylidene OA-6129B$_2$ was dissolved in 4 ml of nitromethane, and 44 μl (0.36 mmole) of tetramethylguanidine was added at −25° C. They were reacted at this temperature for 30 minutes. The reaction mixture was poured into 5 ml of ethyl acetate containing 45 mg of oxalic acid, and washed three times with water. The organic layer was dried over anhydrous sodium sulfate, and concentrated to dryness under reduced pressure. The residue was dissolved in a small amount of methylene chloride, and charged onto a column of Sephadex LH-20 (1.2 cm×90 cm). The column was developed with acetone, and fractions which showed an ultraviolet absorption at an Rf value of 0.59 in silica gel thin-layer chromatography developed with benzene/acetone (1/1) were collected and concentrated to dryness under reduced pressure to give 15 mg (yield 54%) of the title compound having the following physico-chemical properties.

(1) IR spectrum: $\nu_{max}^{CHCl_3}$ cm$^{-1}$: 1780 (β-lactam), 1720 (ester), 1555, 1520, 1350 (nitro).

(2) UV spectrum: $\lambda_{max}^{CHCl_2}$ nm(ε): 268 (13100).

(3) NMR spectrum (CDCl$_3$, TMS)δ: 1.37 (3H, d, J=6.5 Hz, CH$_3$—CH), 2.98 (2H, d, like, J=9.0 Hz, C—4H$_2$), 3.30 (1H, m, C—6H), 3.85–4.35 (2H, m, C—5H, CH$_3$—C$\underline{H}$), 5.14 (1H, d, J=14.0 Hz, C$\underline{H}$H—Ar), 5.29 (1$\underline{H}$, d, J=15.0 Hz, C$\underline{H}$H—NO$_2$), 5.40 (1$\overline{H}$, d, J=14.0 Hz, CH$\underline{H}$—Ar), 5.66 (1H, d, J=15.0 Hz, CH$\underline{H}$—NO$_2$), 7.50 (2$\overline{H}$, d, J=8.5 Hz, Ar.$\underline{H}$), 8.09 (2H, d, J=8.5 Hz, Ar.$\underline{H}$).

EXAMPLE 6 p-Nitrobenzyl 6-ethyl-3-oxycyano-7-oxo-1-azabicyclo[3.2.0]hept-2-ene-2-carboxylate

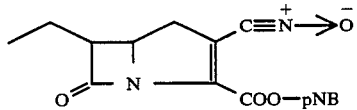

41 mg (0.11 mmole) of p-nitrobenzyl 6-ethyl-3-nitromethyl-7-oxo-1-azabicyclo[3.2.0]hept-2-ene-2-carboxylate obtained by the method of Example 3 was dissolved in 5 ml of DMF, and the solution was cooled to 0° C. Triethylamine (38 μl; 0.22 mmole) and methyl chloroformate (20 μl; 0.22 mmole) were added, and the reaction was carried out at the above temperature for 30 minutes. The reaction mixture was poured into ethyl acetate, and washed with water. The organic layer was dried over anhydrous sodium sulfate and concentrated to dryness under reduced pressure. The residue was dissolved in a small amount of methylene chloride, and adsorbed onto a column of 5 g of silica gel. The column was eluted with benzene/acetone mixtures at mixing ratios of 20/1 and 10/1. Fractions which showed an ultraviolet absorption at an Rf value of 0.40 in silica gel thin-layer chromatography deveoped with benzene-/acetone (10/1) were collected and concentrated to dryness under reduced pressure to give 20 mg of the title compound having the following physico-chemical properties.

(1) IR spectrum: $\nu_{max}^{CHCl_3}$ cm$^{-1}$: 2295 (nitrile), 1792 ($\beta$-lactam), 1730 (ester), 1525, 1355 (nitro).

(2) UV spectrum: $\lambda_{max}^{CHCl_2}$ nm($\epsilon$): 324 (10600), 267 (12000).

(3) NMR spectrum (CDCl$_3$, TMS)$\delta$: 1.02 (3H, t, J=7.5 Hz, CH$_3$—CH$_2$), 1.87 (2H, m, CH$_3$—CH$_2$), 2.98 (1H, dd, J=10.0 Hz, J=19.0 Hz, C—4HH), 3.17 (1H, dd, J=10.0 Hz, J=19.0 Hz, C—4HH), 3.28 (1H, m, C—6H), 4.08 (1H, dt, J=3.0 Hz, J=10 Hz, C—5H), 5.32 (1H, d, J=10.0 Hz, CHH—Ar), 5.51 (1H, d, J=14.0 Hz, CHH—Ar), 7.63 (2H, d, J=9.0 Hz, Ar.H), 8.24 (2H, d, J=9.0 Hz. Ar.H).

EXAMPLE 7 p-Nitrobenzyl 6-ethyl-3-[4,5-bis(methoxycarbonyl)-isoxazol-3-yl]-7-oxo-1-azabicyclo[3.2.0]hept-2-ene-2-carboxylate

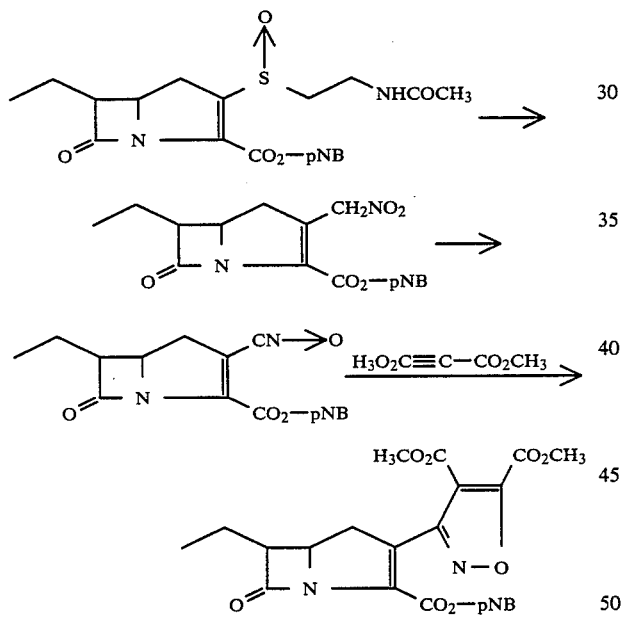

50 mg (0.111 mmole) of PS-5.p-nitrobenzyl ester.S-oxide was dissolved in 9 ml of nitromethane, and at −30° C., 63.9 mg (0.55 mmole) of tetramethylguanidine was added. They were reacted at the above temperature for 30 minutes. The reaction mixture was diluted with 100 ml of ethyl acetate containing 100 mg of oxalic acid, washed with three 50 ml portions of a saturated aqueous solution of sodium chloride, and dried over anhydrous sodium sulfate. The solvent was evaporated under reduced pressure. The resulting oily product was dissolved in 10 ml of DMF. The solution was cooled with ice, and 42 mg (0.3 mmole) of triethylamine and 15.4 µl (0.2 mmole) of methyl chloroformate were added. They were reacted for 30 minutes. At the above temperature, 19.5 µl (0.159 mmole) of methyl acetylenedicarboxylate was added. The reaction temperature was raised to room temperature, and the reaction was carried out for 4 hours. The reaction mixture was diluted with 50 ml of benzene, and washed with three 20 ml portions of a saturated aqueous solution of sodium chloride. The benzene layer was dried over anhydrous sodium sulfate, and the solvent was evaporated under reduced pressure. The residue was purified on a silica gel column using benzene/acetone (50/1, v/v) as a developing solvent to give 20 mg of the title compound having the following physico-chemical properties.

(1) IR spectrum: $\nu_{max}^{CHCl_3}$ cm$^{-1}$: 1790 ($\beta$-lactam), 1740 (ester), 1525, 1355 (nitro).

(2) UV spectrum: $\lambda_{max}^{THF}$ nm($\epsilon$): 268 (13400), 260 (12900), 253 (12000), 248 (11300).

(3) NMR spectrum (CDCl$_3$)$\delta$: 1.07 (3H, t, J=7 Hz, CH$_2$CH$_3$), 1.80 (2H, m, CH$_2$CH$_3$), 3.27 (3H, m, C—4H$_2$, C—6H), 3.73 (3H, s, OCH$_3$), 3.97 (3H, s, OCH$_3$), 4.10 (1H, dt, J=3, 9 Hz, C—5H), 5.10 (1H, d, J=14 Hz, CHHAr), 5.30 (1H, d, J=14 Hz, CHHAr), 7.43 (2H, d, J=9 Hz, ArH), 8.13 (2H, d, J=9 Hz, ArH).

(4) Mass (m/z): 499 (M+), 4.29 (M+—EtCH=C=O).

EXAMPLE 8 p-Nitrobenzyl 6-ethyl-3-(5-methoxycarbonylisoxazolin-3-yl)-7-oxo-1-azabicyclo[3.2.0]hept-2-ene-2-carboxylate

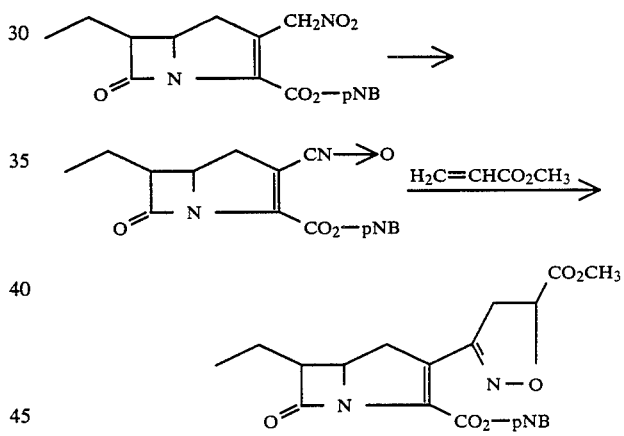

The 3-nitromethyl derivative synthesized in the same way as in Example 3 using 50 mg of PS-5.p-nitrobenzyl ester.S-oxide was dissolved in 5 ml of DNF, and under ice cooling, 15.4 µl (0.2 mmole) of methyl chloroformate and 42 µl of triethylamine were added. They were reacted for 30 minutes. At the same temperature, 25.8 mg (0.3 mmole) of methyl acrylate was added, and the reaction was carried out at room temperature for 4 hours. The reaction mixture was diluted with 30 ml of benzene, washed with a saturated aqueous solution of sodium chloride, and dried over anhydrous sodium sulfate. The solvent was evaporated under reduced pressure. The resulting oily product was purified on a silica gel column using benzene/acetone (25/1, v/v) as a developing solvent to give 25 mg of the title compound having the following physico-chemical properties.

(1) IR spectrum: $\nu_{max}^{CHCl_3}$ cm$^{-1}$: 1785 ($\beta$-lactam), 1740 (ester), 1525, 1350 (nitro). (2) UV spectrum: $\nu_{max}^{THF}$ nm($\epsilon$): 325 (12300), 269 (12000), 262.5 (14200), 257.5 (13600), 251 (12200).

(3) NMR spectrum (CDCl₃)δ: 1.05 (3H, t, J=7 Hz, CH₂CH₃), 1.85 (2H, m, CH₂CH₃), 3.00-3.80 (5H, m, C—4H₂, C—6H, C—4'H₂), 3.75 (3H, s, OCH₃), 3.93 (1H, dt, J=3, 9 Hz, C—5H), 5.10 (1H, m, C—5'H), 5.20 (1H, d, J=14 Hz, CHHAr), 5.45 (1H, d, J=14 Hz, CHHAr), 7.60 (2H, d, J=9 Hz, ArH), 8.20 (2H, d, J=9 Hz, ArH).

(4) Mass (m/z): 443 (M+), 374, 314.

EXAMPLE 9 p-Nitrobenzyl 6-ethyl-3-(4-methyl-5-phenylisoxadiazolin-3-yl)-7-oxo-1-azabicyclo[3.2.0]hept-2-ene-2-carboxylate

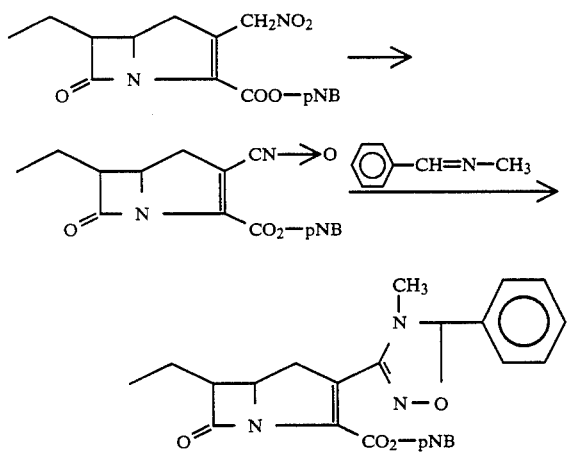

The 3-nitromethyl derivative synthesized in the same way as in Example 3 using 50 mg of PS-5.p-nitrobenzyl ester.S-oxide was dissolved in 5 ml of DMF, and under ice cooling, 42 μl of triethylamine and 15.4 μl of methyl chloroformate were added. They were reacted for 30 minutes. At the same temperature, 47.6 mg (0.4 mmole) of benzylidenemethylamine was added, and the reaction was carried out at room temperature for 4 hours. The reaction mixture was diluted with 20 ml of benzene, washed with a saturated aqueous solution of sodium chlride, and dried over anhydrous sodium sulfate. The solvent was evaporated under reduced pressure. The resulting oily product was purified on a column of silica gel (CC-7; Mallinckrodt Chemical Works) using benzene/acetone (50/1, v/v) as a developing solvent to give 18 mg of the title compound having the following physico-chemical properties.

(1) IR spectrum: ν$_{max}^{CHCl_3}$ cm⁻¹: 1790 (β-lactam), 1735 (ester), 1525, 1350 (nitro).

(2) UV spectrum: λ$_{max}^{THF}$ nm(ε): 270 (11000), 264 (10700), 261 (10000), 255 (8800).

(3) NMR (CDCl₃)δ: 1.03 (3H, t, J=7 Hz, CH₂CH₃), 1.80 (2H, m, CH₂CH₃), 2.50 (3H, s, N—CH₃), 3.16 (3H, m, C—4H₂, C—6H), 4.06 (1H, m, C—5H), 5.26 (1H, d, J=14 Hz, CHHAr), 5.43 (1H, d, J=14 Hz, CHHAr), 5.83, 5.90 (1H, s, C—5'H), 7.33 (5H, m, ArH), 7.63 (2H, d, J=9 Hz, ArH), 8.13 (2H, d, J=9 Hz, ArH).

(4) Mass (m/z): 476 (M+), 406 (M+—EtCH=C=O).

What is claimed is:

1. A compound represented by the following formula:

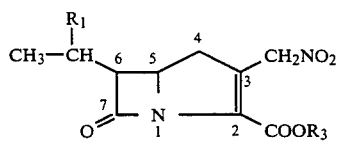

wherein R₁ represents hydrogen or hydroxyl and R₃ represents hydrogen, lower alkyl or lower alkyl substituted by 1 to 3 phenyl groups which phenyl groups are unsubstituted or are substituted by at least one substituent selected from halogen, lower alkyl, lower alkoxy, phenoxy, lower haloalkyl, C₁-C₁₀ alkanoyloxy, benzoyloxyl, lower alkanoylamino, benzoylamino, carboxy, lower alkoxycarbonyl, hydroxy, and nitro.

2. A compound according to claim 1, said compound being p-nitrobenzyl 6-ethyl-3-nitromethyl-7-oxo-1-azabicyclo[3.2.0]hept-2-ene-2-carboxylate, or p-nitrobenzyl 6-(1-hydroxyethyl)-3-nitromethyl-7-oxo-1-azabicyclo[3.2.0]hept-2-ene-2-carboxylate.

3. A process for producing the compound of the formula

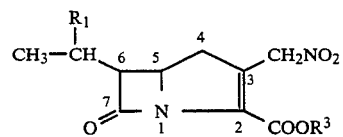

wherein R₁ represents hydrogen or hydroxyl and R₃ represents hydrogen, lower alkyl or lower alkyl substituted by 1 to 3 phenyl groups which phenyl groups are unsubstituted or are substituted by at least one substituent selected from halogen, lower alkyl, lower alkoxy, phenoxy, lower haloalkyl, C₁-C₁₀ alkanoyloxy, benzoyloxyl, lower alkanoylamino, benzoylamino, carboxy, lower alkoxycarbonyl, hydroxy, and nitro which comprises reacting a compound of the following formula

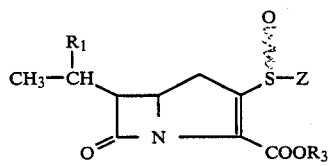

wherein R₁ and R₃ are as defined above, and Z represents group of the formula —CH₂CH₂NHCOCH₃ or a group of the formula

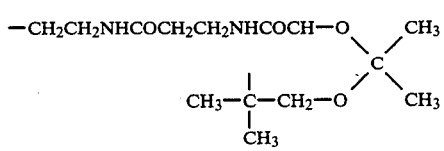

with nitromethane in the presence of a base.

* * * * *